United States Patent
Wexler et al.

(10) Patent No.: US 9,025,016 B2
(45) Date of Patent: May 5, 2015

(54) SYSTEMS AND METHODS FOR AUDIBLE FACIAL RECOGNITION

(71) Applicants: Yonatan Wexler, Jerusalem (IL); Amnon Shashua, Zion (IL)

(72) Inventors: Yonatan Wexler, Jerusalem (IL); Amnon Shashua, Zion (IL)

(73) Assignee: OrCam Technologies Ltd., Jerusalem (IL)

( * ) Notice: Subject to any disclaimer, the term of this patent is extended or adjusted under 35 U.S.C. 154(b) by 0 days.

(21) Appl. No.: 14/135,727

(22) Filed: Dec. 20, 2013

(65) Prior Publication Data

US 2014/0267642 A1 Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*G06K 9/00* (2006.01)
*G09B 21/00* (2006.01)
(Continued)

(52) U.S. Cl.
CPC ............ *G09B 21/001* (2013.01); *G09B 21/006* (2013.01); *A61F 9/08* (2013.01); *G06K 9/00671* (2013.01); *G09B 21/00* (2013.01); *G09B 21/003* (2013.01); *H04N 5/23229* (2013.01); *G08B 3/10* (2013.01); *G08B 6/00* (2013.01); *H04N 5/23232* (2013.01); *G06F 17/2765* (2013.01); *G06K 9/74* (2013.01); *G10L 13/043* (2013.01);
(Continued)

(58) Field of Classification Search
CPC ............................. G06K 9/00221; G06F 1/163
See application file for complete search history.

(56) References Cited

U.S. PATENT DOCUMENTS 6,115,482 A 9/2000 Sears et al.
2005/0208457 A1* 9/2005 Fink et al. .................... 434/112
(Continued)

FOREIGN PATENT DOCUMENTS

EP 2065871 6/2009
EP 2 490 155 8/2012

OTHER PUBLICATIONS

U.S. Appl. No. 14/136,438, filed Dec. 20, 2013, entitled "Apparatus, Method, and Computer Readable Medium for Expedited Text Reading Using Staged OCR Technique."
(Continued)

*Primary Examiner* — Joseph Ustaris
*Assistant Examiner* — Mikhail Itskovich
(74) *Attorney, Agent, or Firm* — Finnegan, Henderson, Farabow, Garrett & Dunner, LLP

(57) ABSTRACT

A device and method are provided for audible facial recognition. In one implementation, an apparatus for aiding a visually impaired user to identify individuals is provided. The apparatus may include a portable image sensor configured to be worn by the visually impaired user and to capture real-time image data from an environment of the user. The apparatus may also include at least one portable processor device configured to determine an existence of face-identifying information in the real-time image data, and access stored facial information and audible indicators. The at least one portable processor device may also be configured to compare the face-identifying information with the stored facial information, and identify a match. Based on the match, the at least one portable processor may be configured to cause an audible indicator to be announced to the visually impaired user.

26 Claims, 22 Drawing Sheets

(51) Int. Cl.
*A61F 9/08* (2006.01)
*H04N 5/232* (2006.01)
*G08B 3/10* (2006.01)
*G08B 6/00* (2006.01)
*G06F 17/27* (2006.01)
*G06K 9/74* (2006.01)
*G10L 13/04* (2013.01)
*G06F 3/16* (2006.01)
*G06F 3/01* (2006.01)
*H04N 5/225* (2006.01)
*G02C 11/00* (2006.01)

(52) U.S. Cl.
CPC .............. *G06F 3/16* (2013.01); *G02C 11/10* (2013.01); *G06F 3/011* (2013.01); *H04N 5/2251* (2013.01); *G06K 9/00221* (2013.01)

(56) References Cited

U.S. PATENT DOCUMENTS

| | | | |
|---|---|---|---|
| 2006/0017810 | A1 | 1/2006 | Kurzweil et al. |
| 2011/0212717 | A1 | 9/2011 | Rhoads et al. |
| 2011/0221656 | A1 | 9/2011 | Haddick et al. |
| 2012/0212499 | A1* | 8/2012 | Haddick et al. .............. 345/589 |
| 2012/0212593 | A1 | 8/2012 | Na'aman et al. |
| 2013/0035742 | A1 | 2/2013 | Talbot et al. |
| 2013/0169536 | A1 | 7/2013 | Wexler et al. |
| 2013/0271584 | A1 | 10/2013 | Wexler et al. |

OTHER PUBLICATIONS

U.S. Appl. No. 14/137,033, filed Dec. 20, 2013, entitled "Apparatus and Method for Providing Failed-Attempt Feedback Using a Camera on Glasses."
U.S. Appl. No. 14/137,263, filed Dec. 20, 2013, entitled "Apparatus and Method for Executing System Commands Based on Captured Image Data."
U.S. Appl. No. 14/135,757, filed Dec. 20, 2013, entitled "Systems and Methods for Automatic Control of a Continuous Action."
U.S. Appl. No. 14/137,373, filed Dec. 20, 2013, entitled "Apparatus and Method for Automatic Action Selection Based on Image Context."
U.S. Appl. No. 14/135,762, filed Dec. 20, 2013, entitled "Systems And Methods For Performing A Triggered Action."
U.S. Appl. No. 14/137,328, filed Dec. 20, 2013, entitled "Apparatus and Method for Performing Actions Based on Captured Image Data."
U.S. Appl. No. 14/135,859, filed Dec. 20, 2013, entitled "Apparatus Connectable to Glasses."
U.S. Appl. No. 14/137,446, filed Dec. 20, 2013, entitled "Apparatus and Method for Hierarchical Object Identification Using a Camera on Glasses."
U.S. Appl. No. 14/135,928, filed Dec. 20, 2013, entitled "Systems and Methods for Processing Images."
U.S. Appl. No. 14/135,775, filed Dec. 20, 2013, entitled "Systems and Methods for Providing Feedback Based on the State of an Object."
U.S. Appl. No. 14/137,522, filed Dec. 20, 2013, entitled "Apparatus and Method for Using Background Change to Determine Context."
U.S. Appl. No. 14/136,545, filed Dec. 20, 2013, entitled "Apparatus, Method, and Computer Readable Medium for Recognizing Text on a Curved Surface."
U.S. Appl. No. 14/137,384, filed Dec. 20, 2013, entitled "Systems and Methods for Audibly Presenting Textual Information Incuded in Image Data."
U.S. Appl. No. 14/136,876, filed Dec. 20, 2013, entitled "Apparatus and Method for Analyzing Images."
Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.
Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).
International Search Report and Written Opinion in International Application No. PCT/IB2014/000925, Mailing date: Aug. 6, 2014 (12 page).
Battaglia et al., "An Open Architecture to Develop a Handheld Device for Helping Visually Impaired People," IEEE Transactions on Consumer Electronics. Aug. 2012, pp. 1086-1093, vol. 58, No. 3.
Jager et al., "A Low-Power, Distributed, Pervasive Healthcare System for Supporting Memory," Proceedings of the International Symposium on Mobile Ad Hoc Networking and Computed, Jan. 1, 2011, pp. 1-7, Paris, France.
Choi et al., "Realtime Training on Mobile Devices for Face Recognition Applications," Pattern Recognition, vol. 44, No. 2, Feb. 1, 2011, pp. 386-400.
Balduzzi et al., "Low-Cost Face Biometry for Visually Impaired Users," Biometric Measurements and Systems for Security and Medical Applications, 2010 IEEE Workshop, Sep. 9, 2010, pp. 45-52.

* cited by examiner

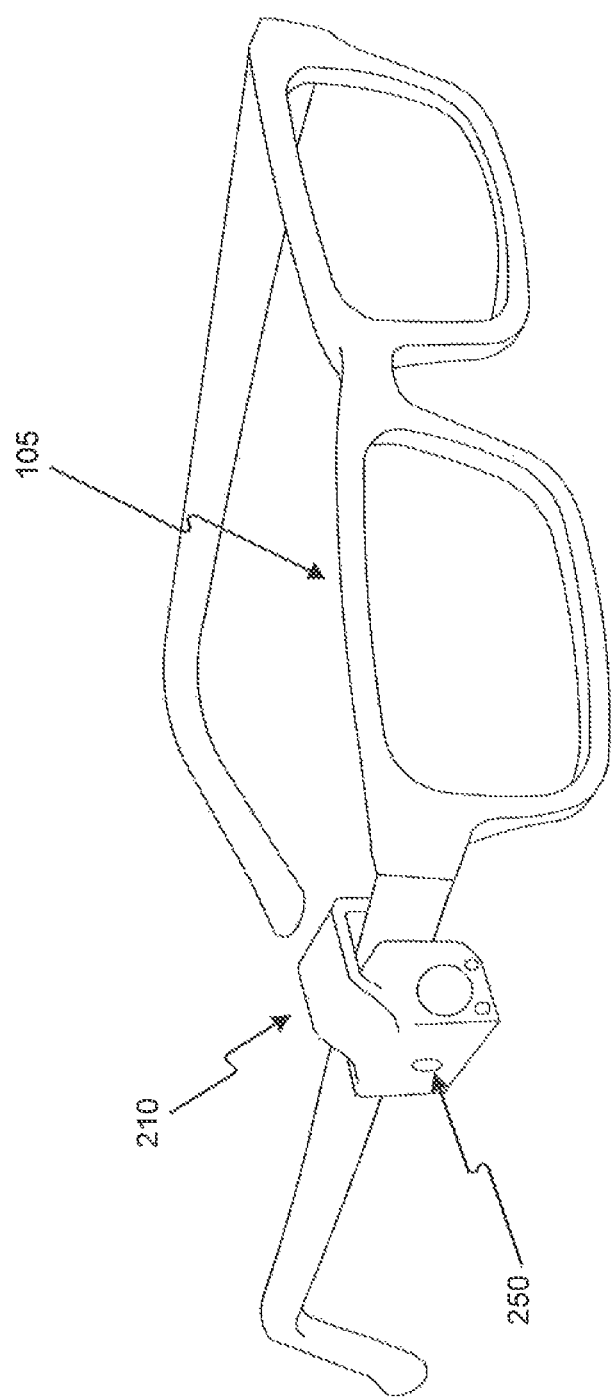

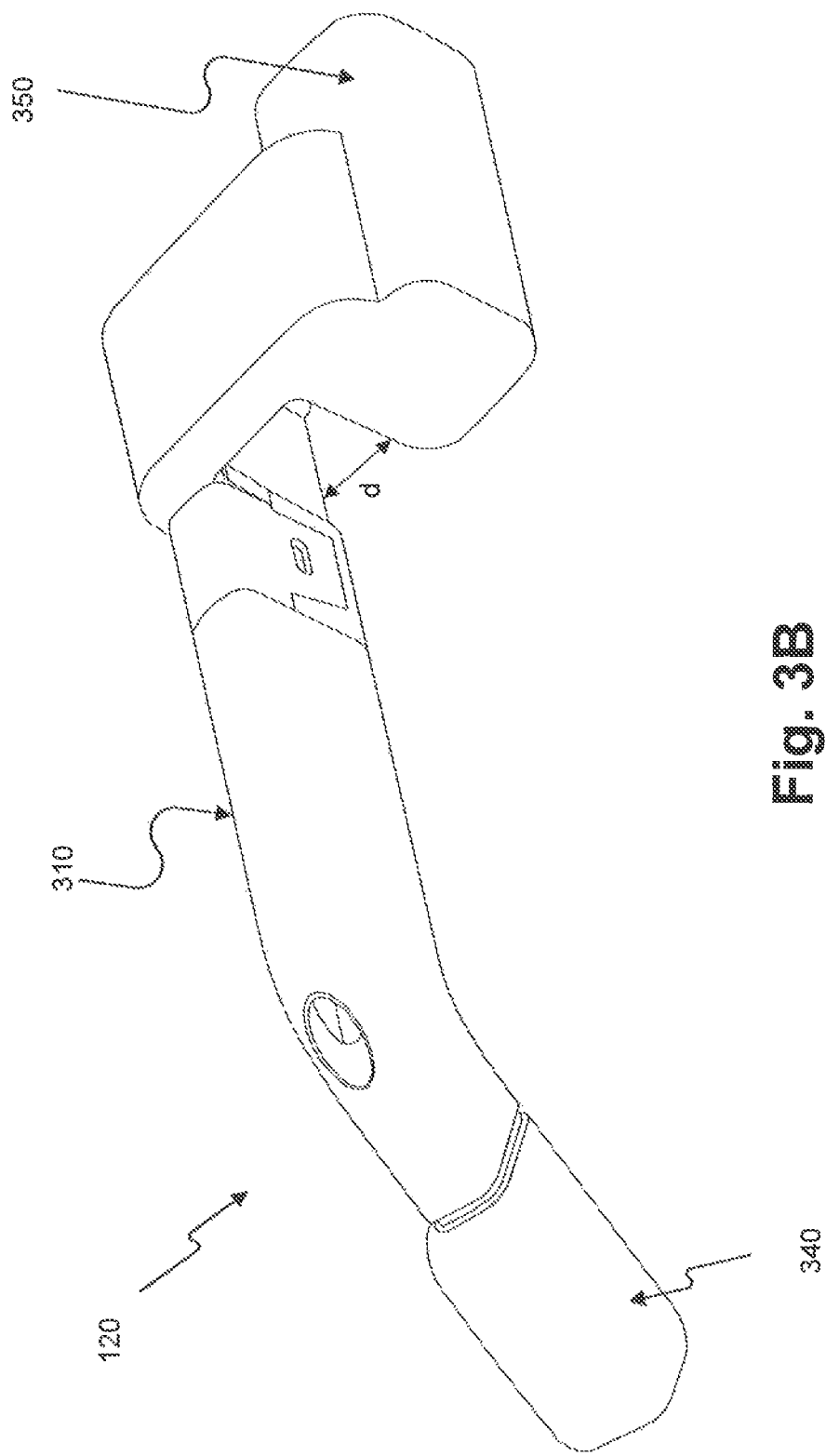

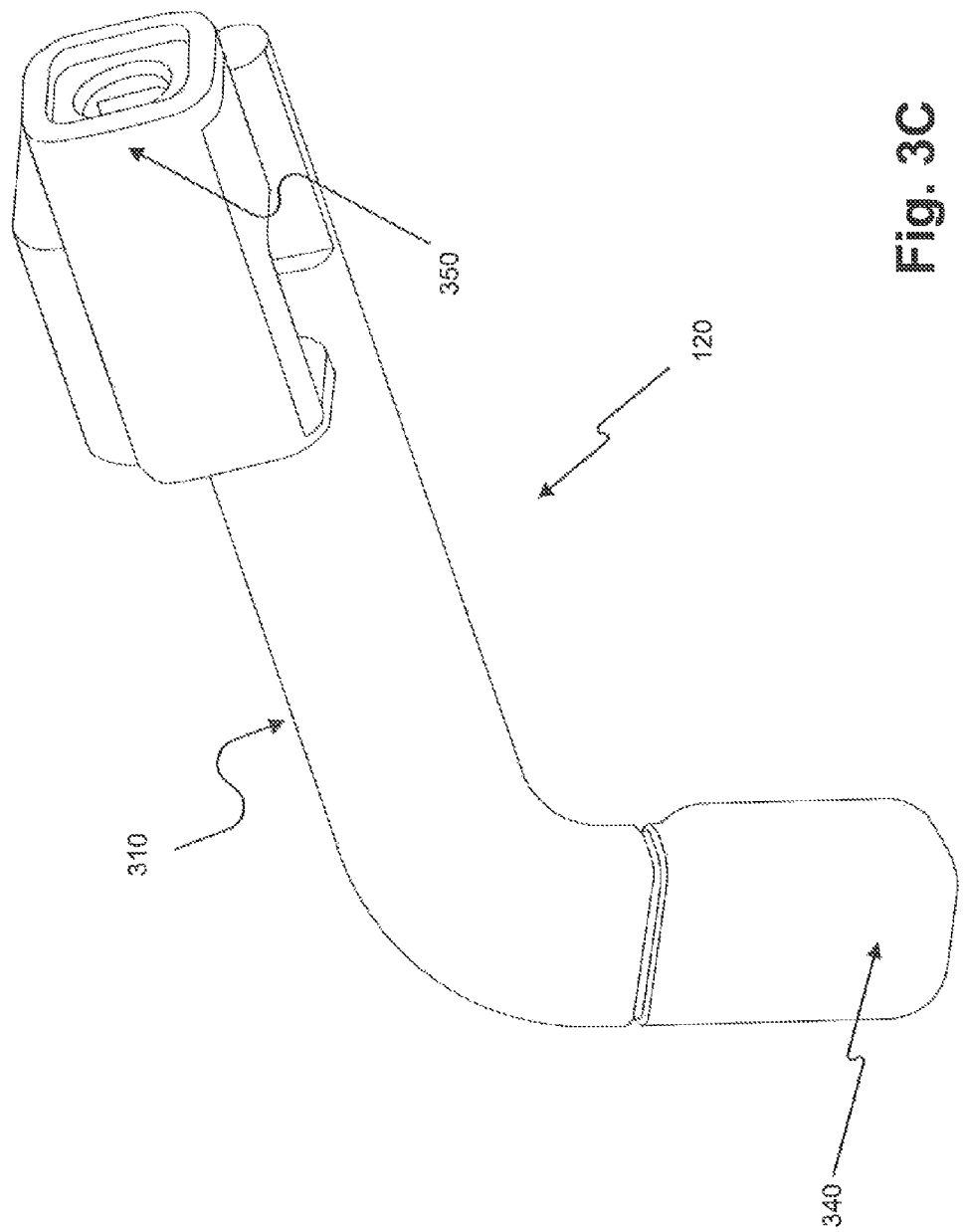

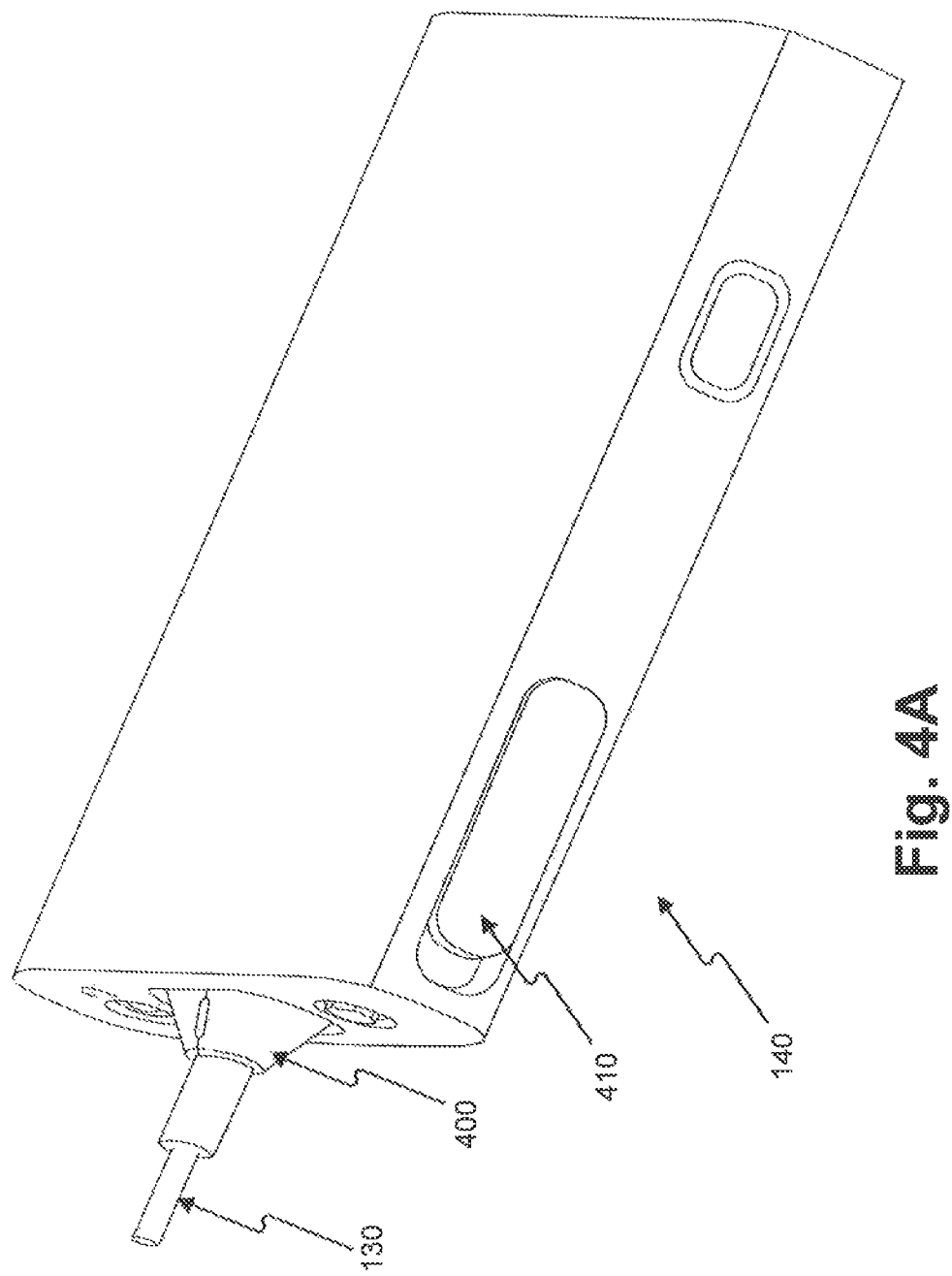

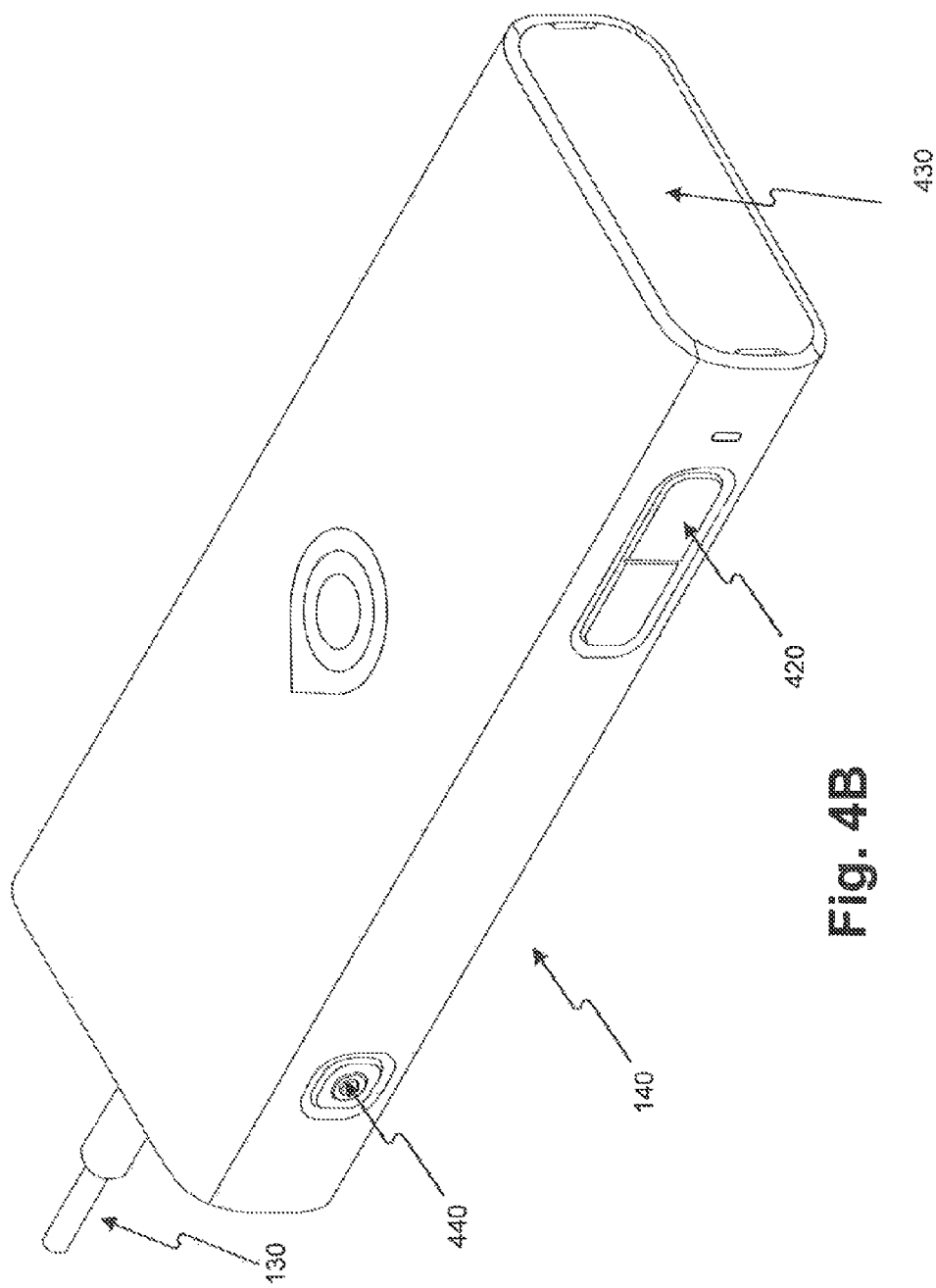

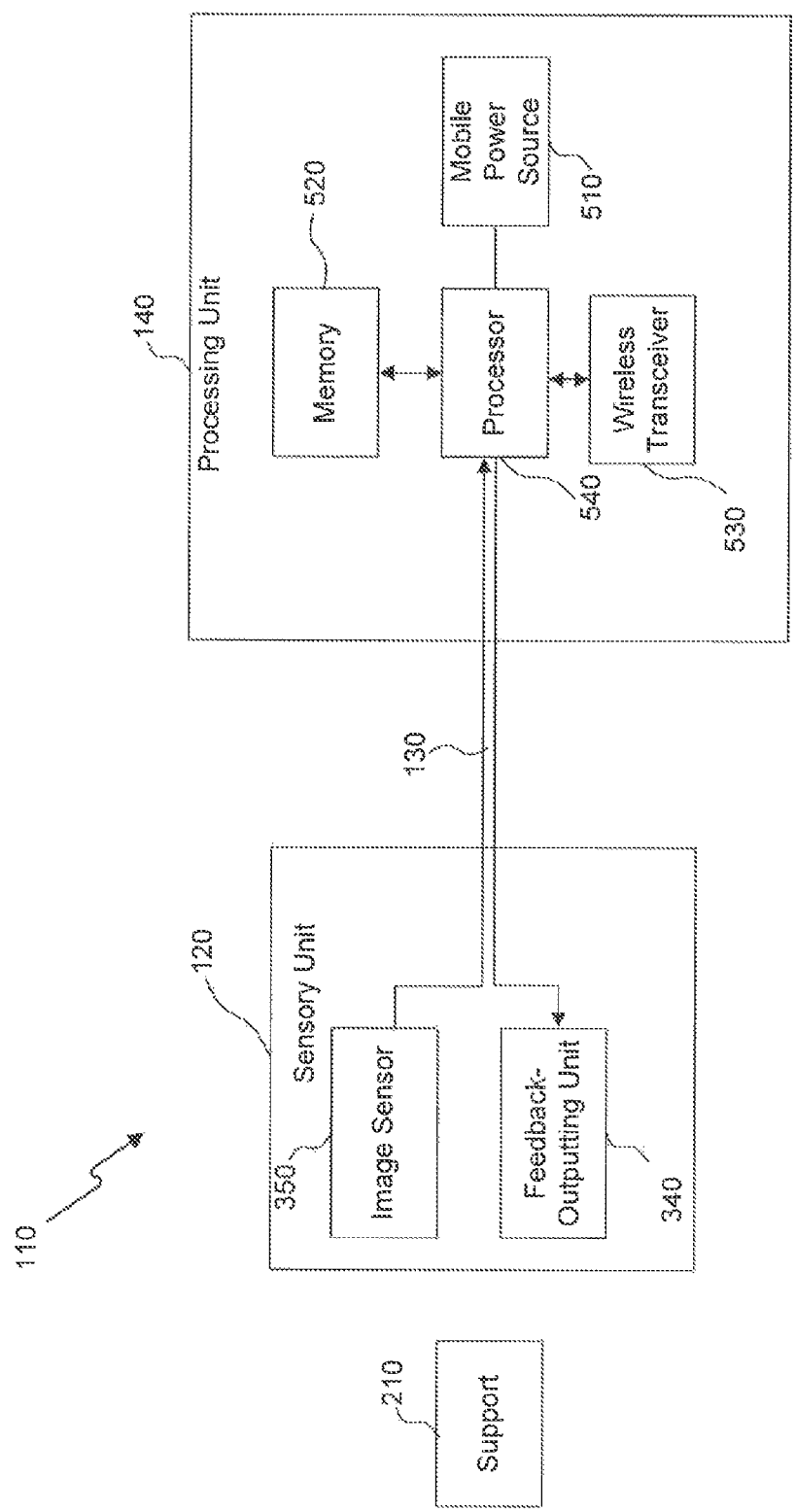

SYSTEMS AND METHODS FOR AUDIBLE FACIAL RECOGNITION

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

1. Technical Field

This disclosure generally relates to devices and methods for providing information to a user. More particularly, this disclosure relates to devices and methods for providing information to a user by processing images captured from the environment of the user.

2. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus for aiding a visually impaired user to identify individuals is disclosed. The apparatus may include a portable image sensor configured to be worn by the visually impaired user and to capture real-time image data from an environment of the user. The apparatus may also include at least one portable processor device configured to determine an existence of face-identifying information in the real-time image data. The portable processor device may also be configured to access at least one database storing facial information associated with selected individuals and audible indicators of identities of the individuals, and compare the face-identifying information in the real-time image data with the stored facial information in the at least one database. The portable processor device may additionally be configured to identify a match between the face-identifying information in the real-time image data and the stored facial information in the at least one database, and, based on the match, cause an audible indicator of an identity of an associated individual to be announced to the visually impaired user.

Consistent with another disclosed embodiment, a software product stored on a non-transitory computer readable medium is provided. The software product may include data and computer implementable instructions for carrying out a method for identifying individuals in an environment of a user. The method may include receiving real-time image data from a portable image sensor configured to be worn by the user and to capture real-time image data from the environment of the user. The method may also include determining an existence of face-identifying information in the real-time image data. The method may further include accessing at least one database storing facial information associated with selected individuals and indicators associated with identities of the selected individuals, and comparing the face-identifying information in the real-time image data with the stored facial information in the at least one database. The method may additionally include identifying a match between the face-identifying information in the real-time image data and the stored facial information in the at least one database. The method may also include outputting to the user an indicator of an associated individual, and withholding outputting of the indicator of the associated individual when the associated individual re-appears in the image data within a predetermined period after the associated individual was initially identified.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 2C is a schematic illustration of the support shown in FIG. 2A mounted on a pair of glasses;

FIG. 3B is a schematic illustration of the sensory unit shown in FIG. 3A from a second viewpoint;

FIG. 3C is a schematic illustration of the sensory unit shown in FIG. 3A from a third viewpoint;

FIG. 4A is a schematic illustration of an example of a processing unit from a first viewpoint;

FIG. 4B is a schematic illustration of the processing unit shown in FIG. 4A from a second viewpoint;

FIG. 5A is a block diagram illustrating an example of the components of an apparatus for aiding persons who have low vision according to a first embodiment;

DETAILED DESCRIPTION

Figure 1:
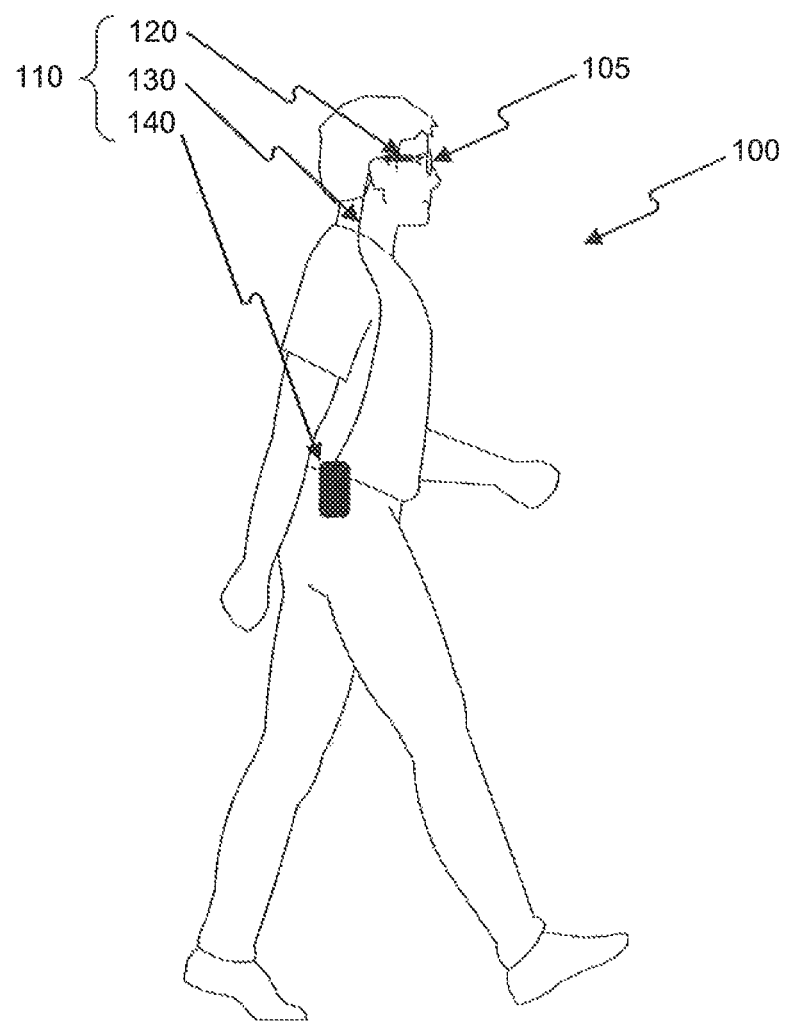
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
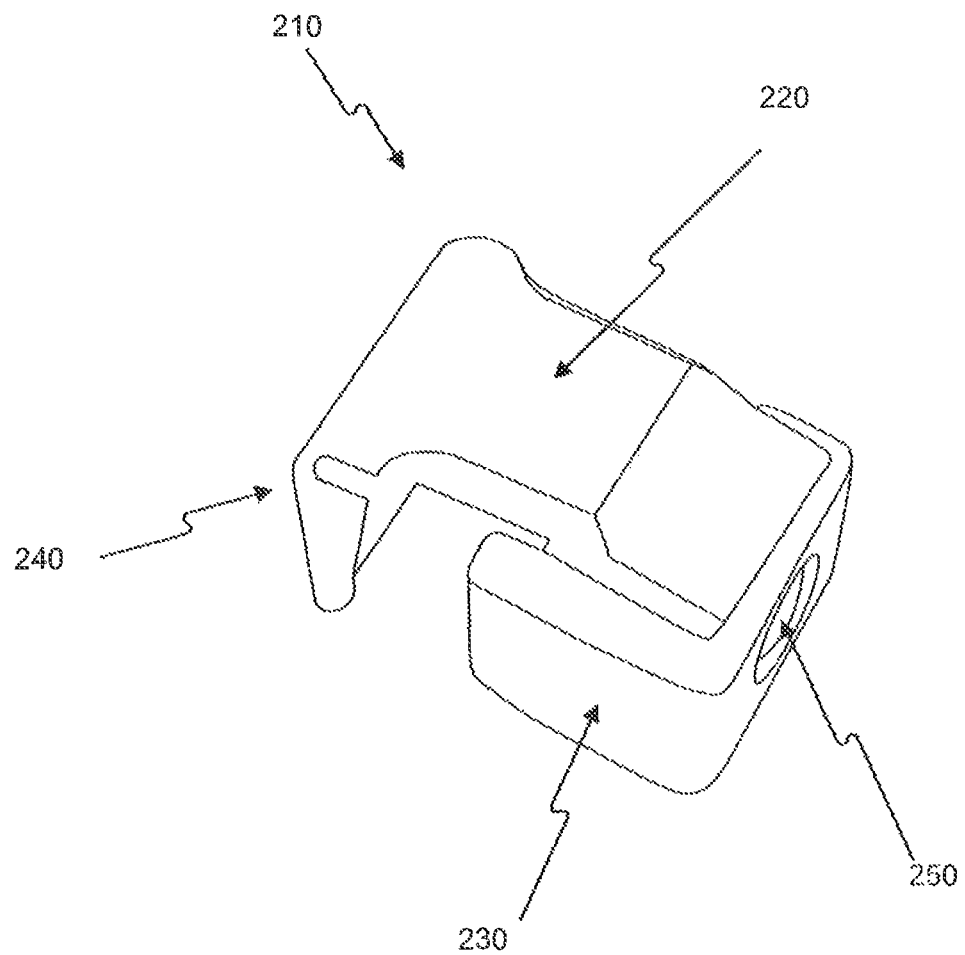
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
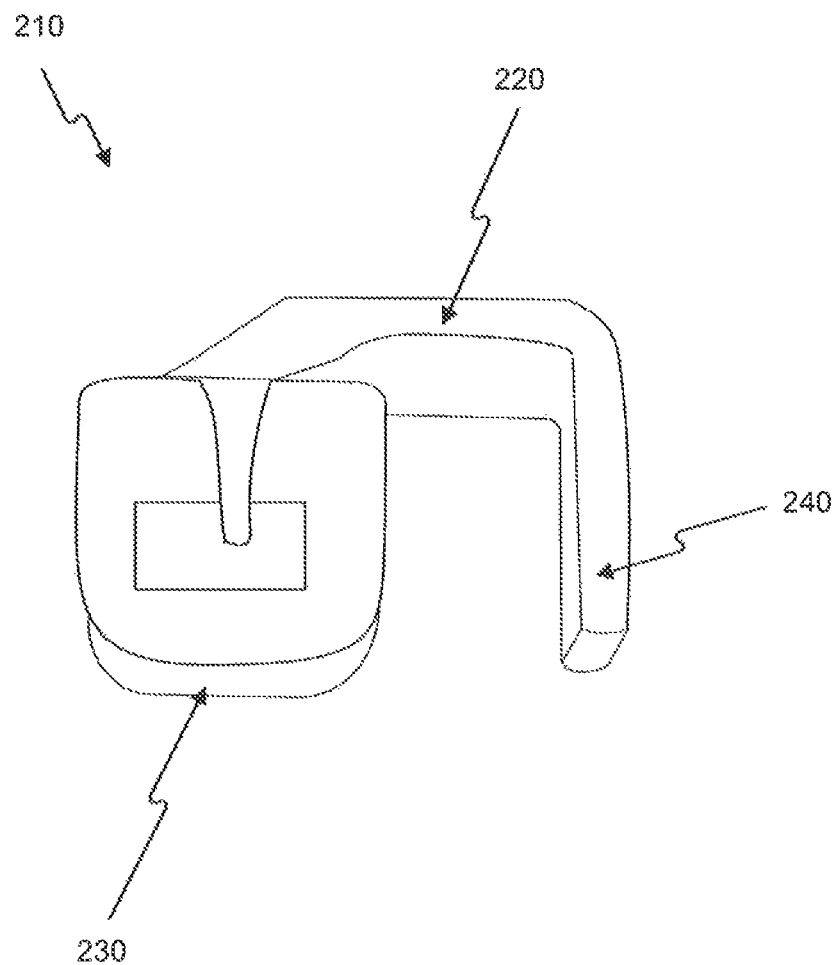
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
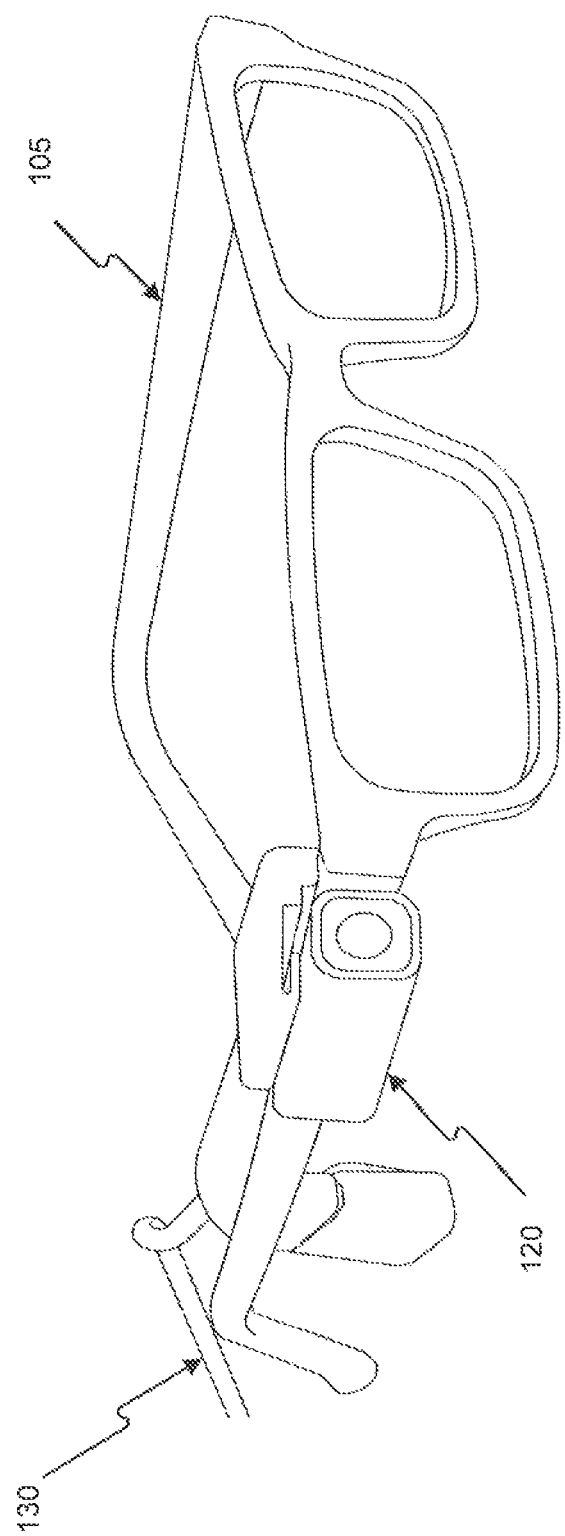
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
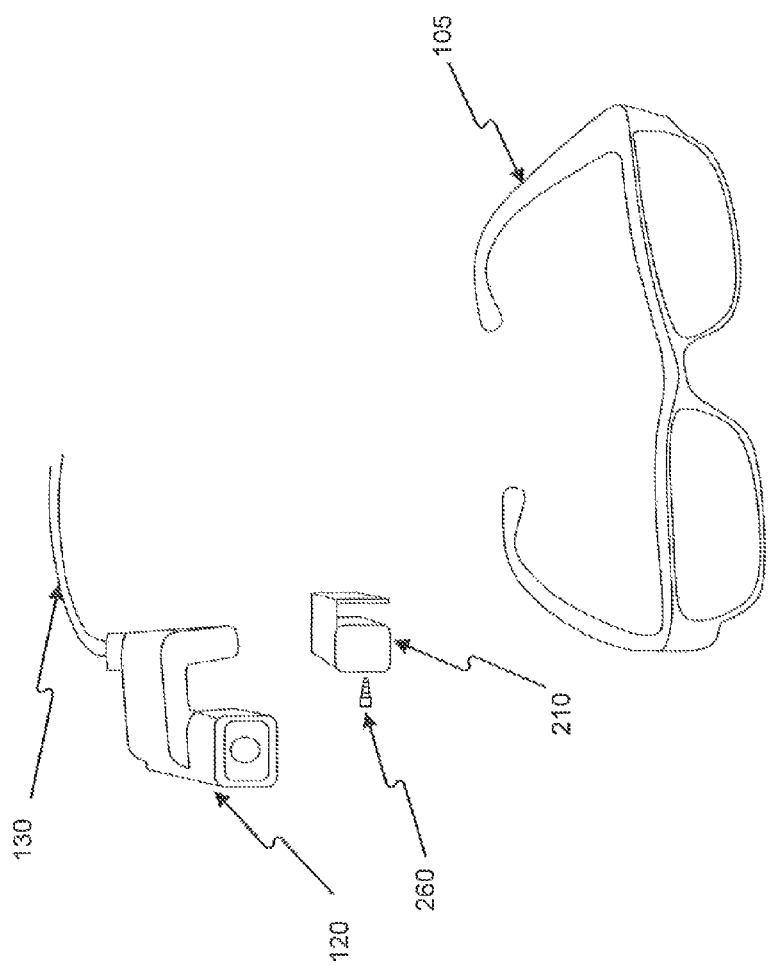
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
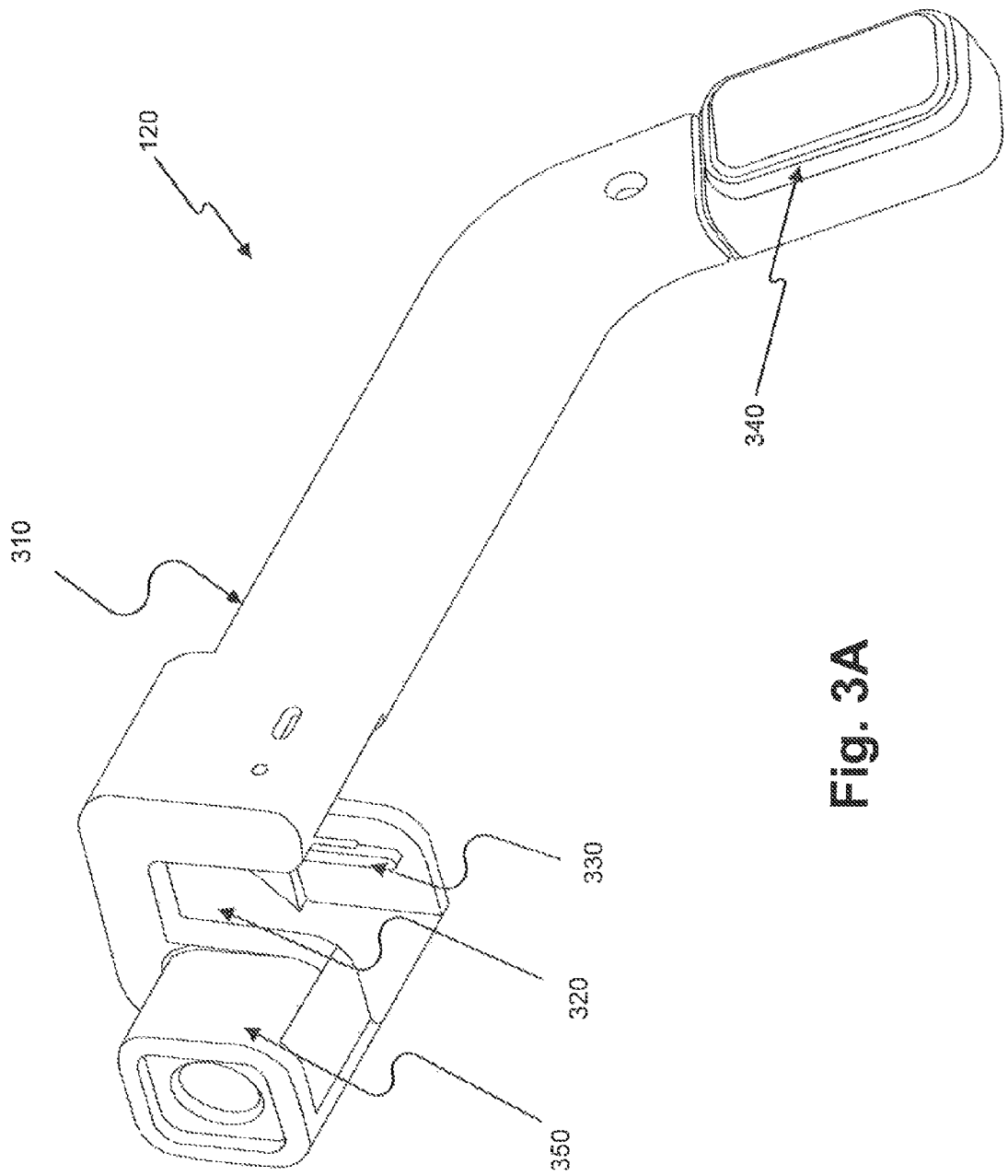
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
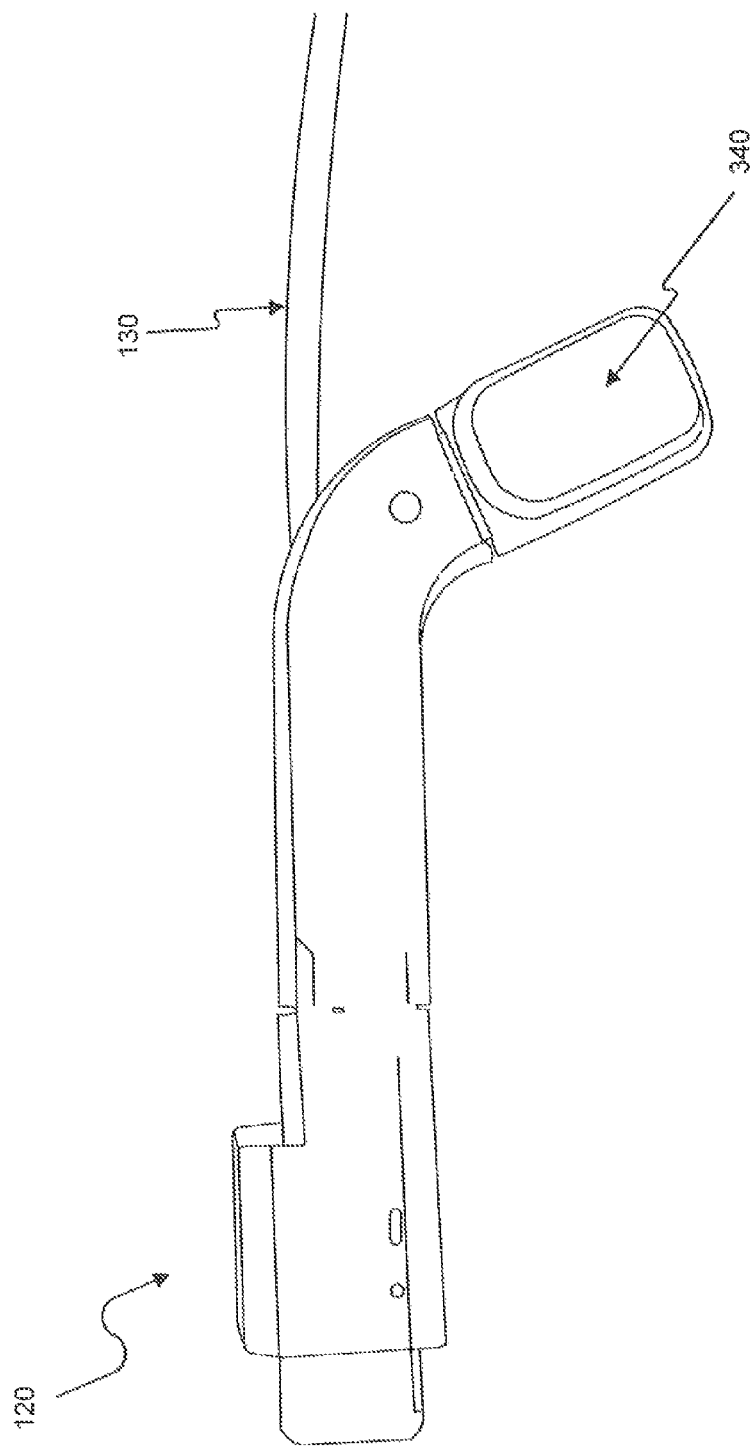
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3O. FIG. 3D shows the side of the U-shaped element that includes feedback-outputting unit 340.

Figure 3E:
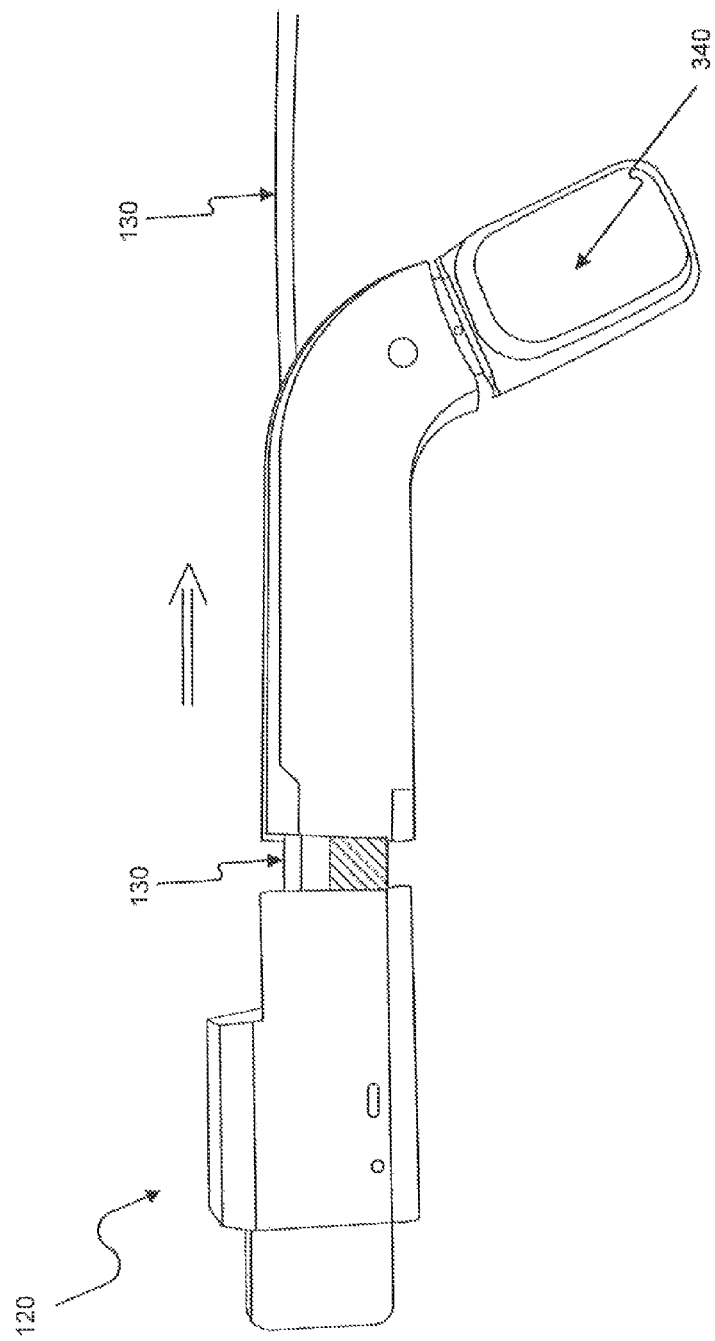
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
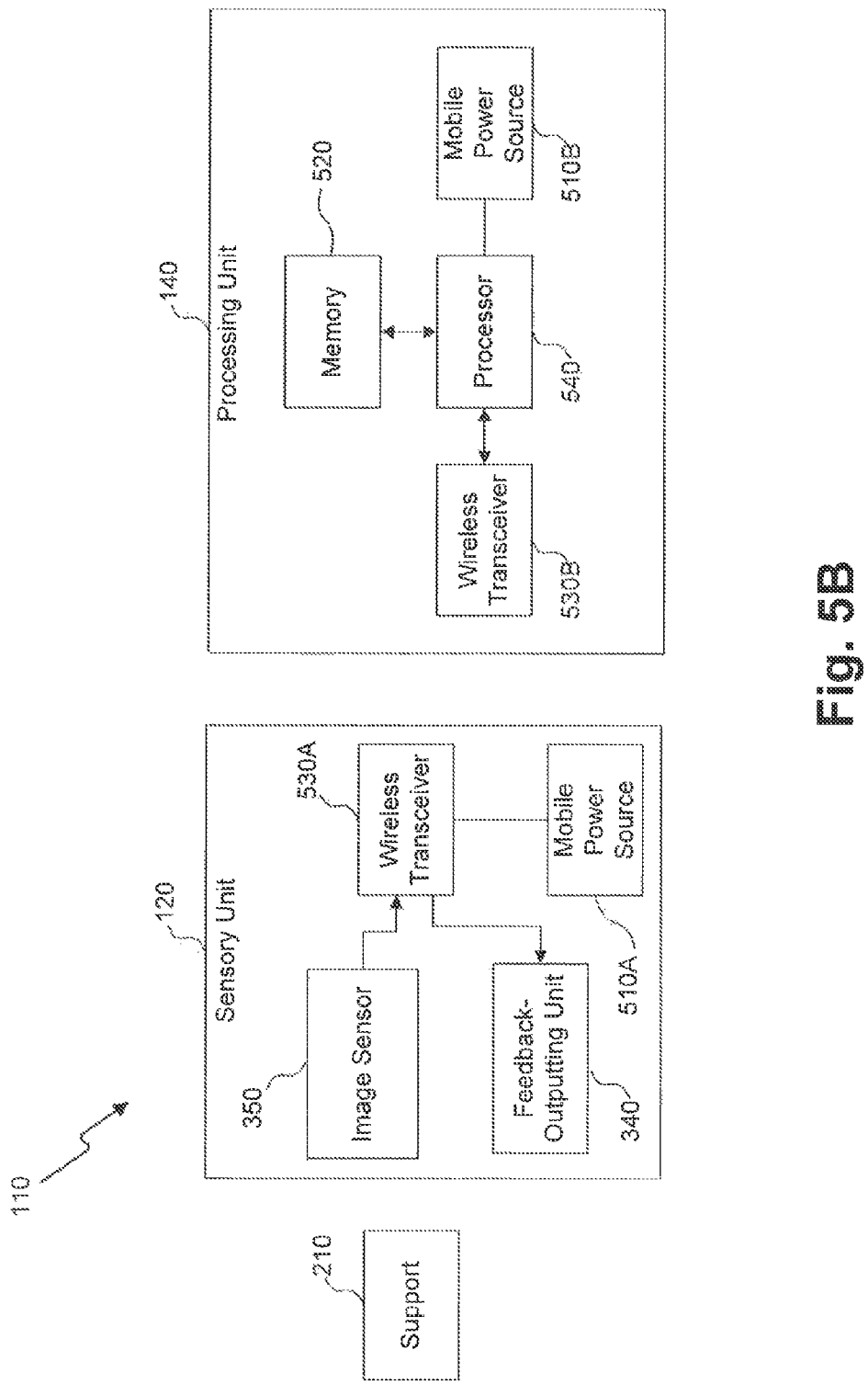
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
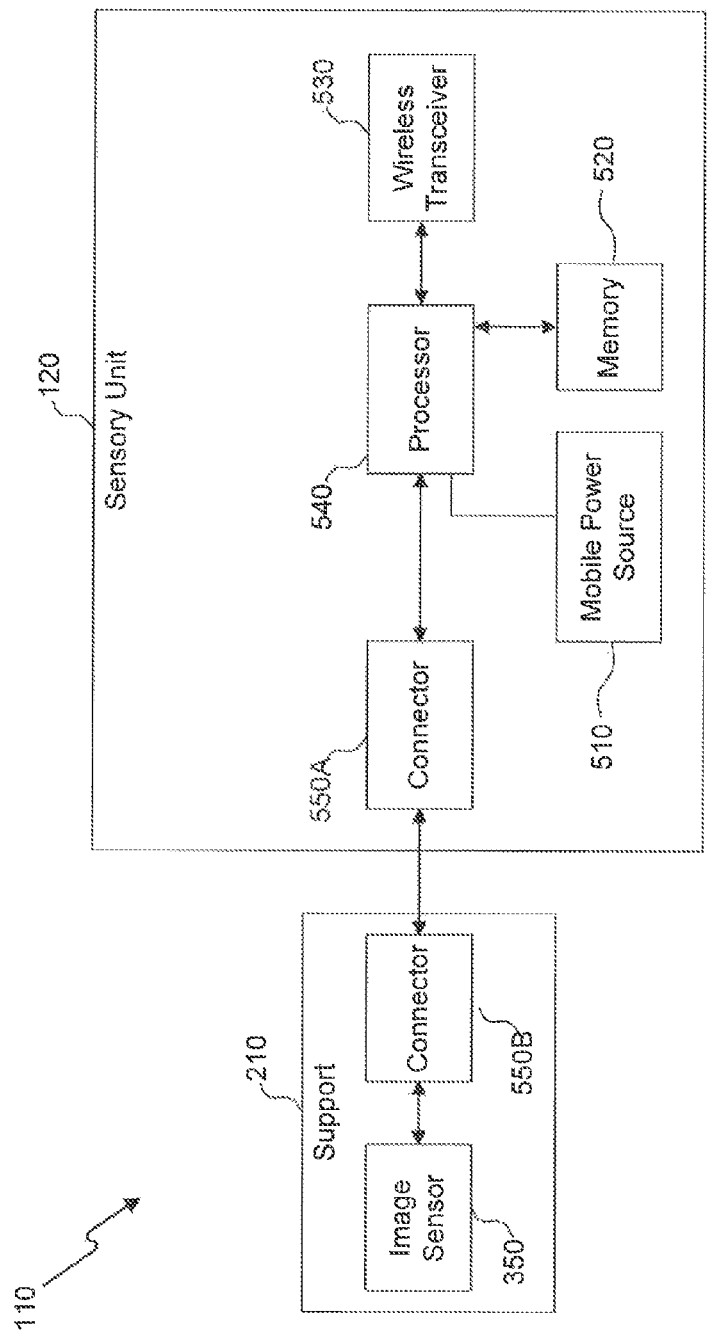
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
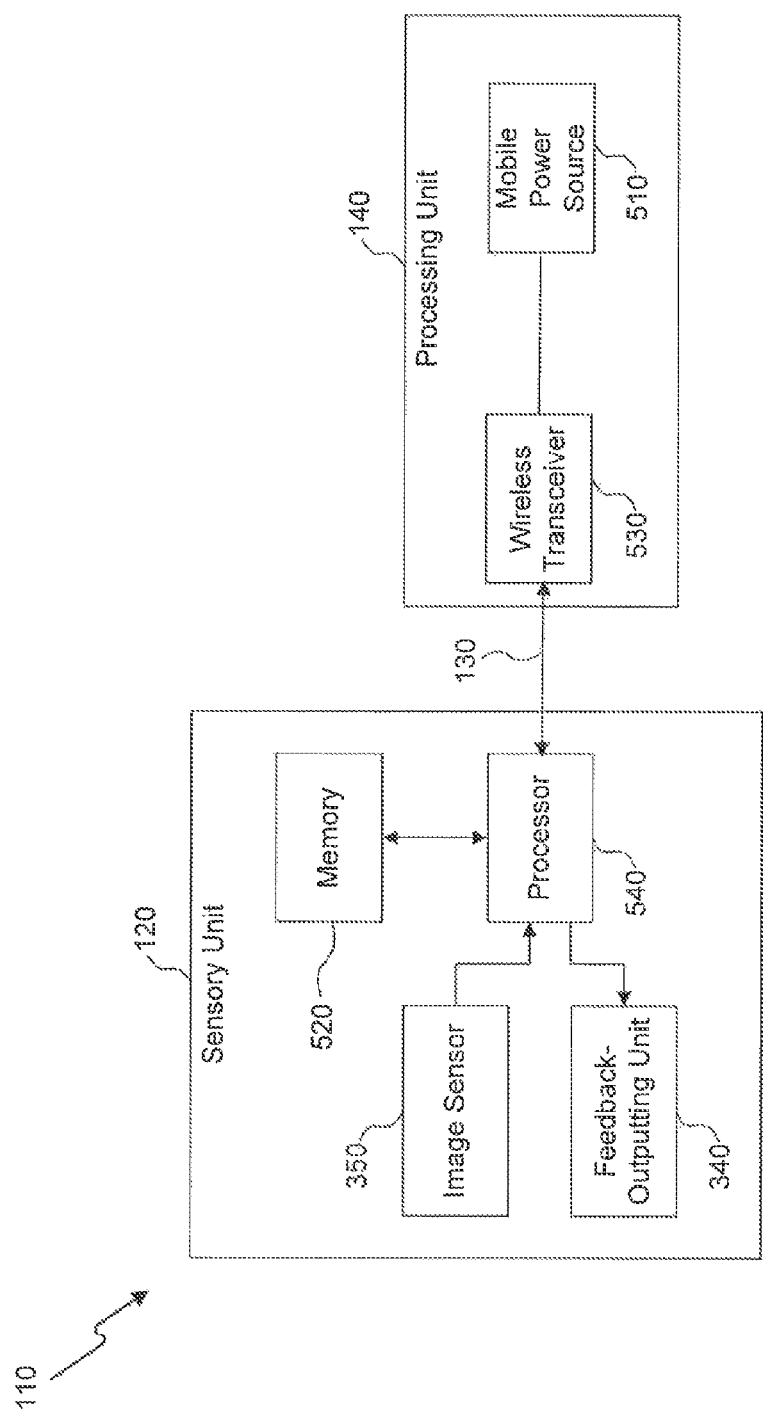
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides an audible facial recognition function. Apparatus 110 may use the audible facial recognition function to identify individuals near a user of apparatus 110. In this way, in situations in which a visually-impaired user of apparatus 110 cannot identify or is unsure of the identity of a person nearby, apparatus 110 may be configured to recognize the individual and announce to the user an identifier of the nearby person.

Figure 6:
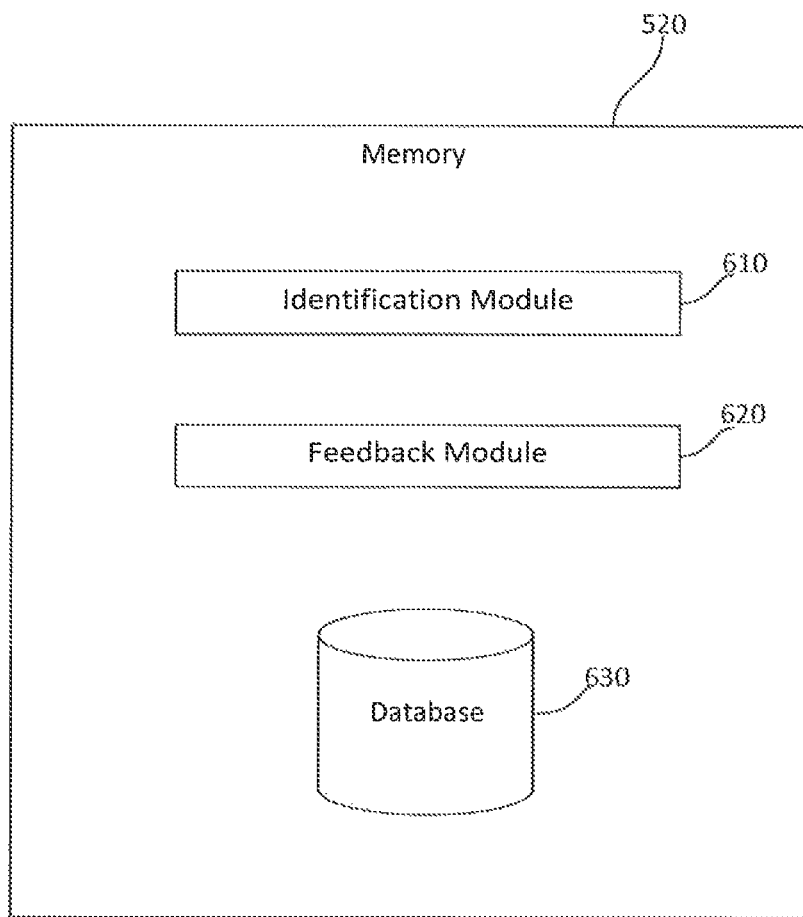
FIG. 6 is a block diagram illustrating an example of a memory configured to provide an audible facial recognition function, consistent with disclosed embodiments.

In some embodiments, memory 520 may include components configured to provide the audible facial recognition function. As shown in FIG. 6, memory 520 may include an identification module 610, a feedback module 620, and a database 630. Identification module 610 may be a component configured to identify a person based on data received from sensory unit 120. Feedback module 620 may be a component configured to interact with a user to provide output to and receive input from the user. Database 630 may be a component configured to store data associated with the audible facial recognition function and provide particular data when requested Identification module 610 and feedback module 620 may be implemented in software, hardware, firmware, a mix of any of those, or the like. For example, if identification module 610 and feedback module 620 are implemented in software, they may be stored in memory 520, as shown in FIG. 6. Other components of processing unit 140 and/or sensory unit 120 may be configured to perform processes to implement and facilitate operations of identification module 610 and feedback module 620. Thus, identification module 610 and feedback module 620 may include software, hardware, or firmware instructions (or a combination thereof) executable by one or more processors (e.g., processor 540), alone or in various combinations with each other. For example, identification module 610 and feedback module 620 may be configured to interact with each other and/or other modules of apparatus 110 to perform functions consistent with disclosed embodiments. In some embodiments, any of the disclosed modules (e.g., identification module 610 and feedback module 620) may each include dedicated sensors (e.g., IR, image sensors, etc.) and/or dedicated application processing devices to perform the functionality associated with each module.

Database 630 may include one or more memory devices that store information and are accessed and/or managed through a computing device, such as processing unit 140. In some embodiments, database 630 may be located in memory 520, as shown in FIG. 6. In other embodiments, database 630 may be located remotely from memory 520, and be accessible to other components of apparatus 110 (e.g., processing unit 140) via one or more wireless connections (e.g., a wireless network). While one database 630 is shown, it should be understood that several separate and/or interconnected databases may make up database 630. Database 630 may include computing components (e.g., database management system, database server, etc.) configured to receive and process requests for data stored in memory devices associated with database 630 and to provide data from database 630.

In some embodiments, database 630 may be configured to store identifying information associated with individual people. For example, database 630 may be configured to store face-identifying information associated with a particular person. For the purposes of this disclosure, "face-identifying information" (also referred to herein as "facial information") may include any identifying information associated with the visual appearance of an individual. In some embodiments, face-identifying information may include information associated with the appearance of a person's face and/or head. In some embodiments, face-identifying information may include any combination of: one or more images of an individual's face, a list of features that describes a face, geometric information extracted from one or more images of a face, image statistics extracted from one or more images of the face, and any other information that can be used for face recognition. Further, in some embodiments, particular face-identifying information may include, for example, face shape information, face size information, facial features (e.g., facial hair, eye color, etc.), size and/or proportion of facial features, skin color, hair style, hair color, piercings, etc. It should be understood, however, that face-identifying information may not be limited to the physical appearance of a person's face. For example, face-identifying information may include information associated with the appearance of one or more other parts of the individual's body (besides the person's face) and/or the appearance of the individual's entire body. In some embodiments, other modalities may also be used to identify the person, such as the individual's voice.

Database 630 may be configured to store face-identifying information for each of any number of different individuals. The face-identifying information for each individual may be derived from image data, such as image data collected by sensory device 120. The face-identifying information may be derived from a single image or multiple images of the individual. Face-identifying information from multiple images of an individual may be compiled and stored in a manner to create a collective and/or composite profile of that individual. For example, database 630 may be configured to store multiple possible hair styles for one individual. Similarly, database 630 may be configured to replace outdated face-identifying information with updated data, such as changes in a person's appearance (due to aging, for example).

Database 630 may also be configured to collect and store one or more identifiers associated with one or more individuals. For example, database 630 may be configured to store one or more identifiers associated with individuals for which face-identifying information is also stored. In some embodiments, identifiers may include any information that may identify an individual to a user of apparatus 110. For example, the identifier may be a person's name. Additionally or alternatively, identifiers may include other identifying information, such as other information about an individual (e.g., nickname, trait, descriptive term, etc.).

In some embodiments, identifiers may include audible identifiers. Audible identifiers may include any data that may be used to produce an audible output to announce information associated with the audible identifier. For example, an audible identifier may include a stored audio recording of identifying information (e.g., an audio recording of a person's name), which may be made either by the user or the individual they are trying to recognize. In another example, an audible identifier may be a text identifier configured to be converted to audio output. Apparatus 110 may be configured to output audible identifiers to a user of apparatus 110, such as via feedback-outputting unit 340. While audible identifiers are described herein, it should be understood that identifiers may be output to a user of apparatus 110 in any other manner, such as by being displayed as text on a display device.

In an exemplary embodiment, database 630 may be configured to associate each stored audible identifier with one or more persons for which face-identifying information is also stored. In this way, apparatus 110 may be configured to receive face-identifying information associated with an individual, match the face-identifying information to stored face-identifying information associated with a particular person, and provide an associated audible identifier to identify the individual.

Figure 7:
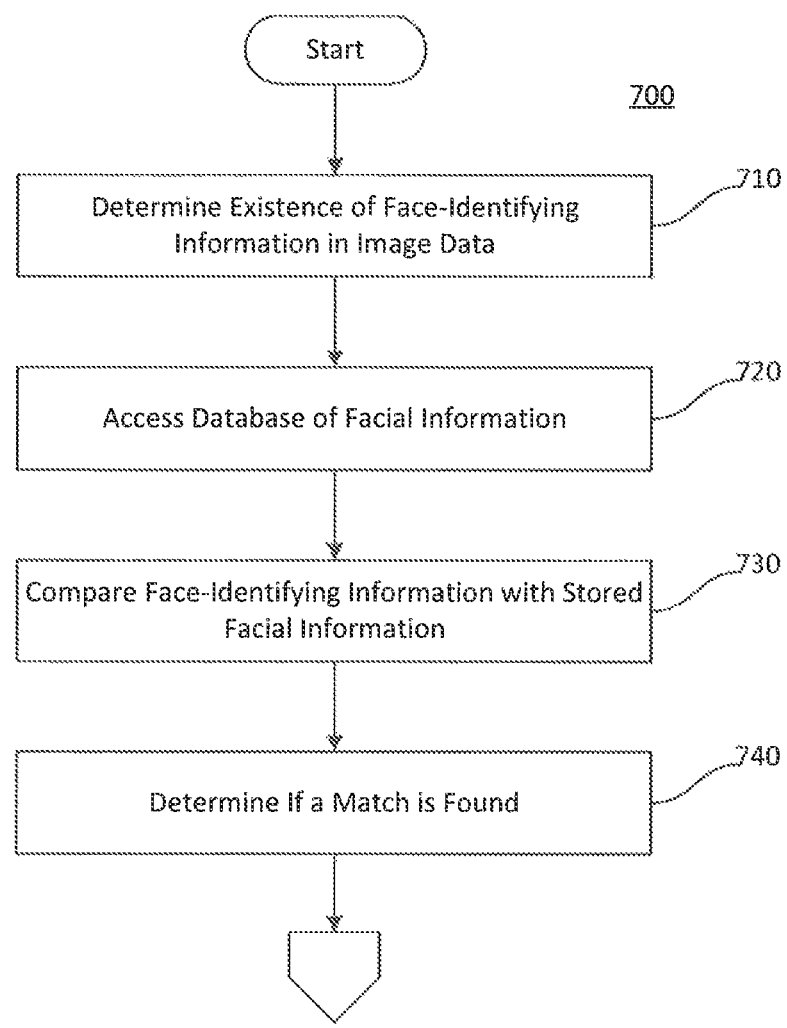
FIG. 7 is a flowchart of an example of a process for determining if an individual is recognized, consistent with disclosed embodiments.

FIGS. 7-10 depict examples of audible facial recognition processes, consistent with disclosed embodiments. FIG. 7 depicts an example of a process 700 for determining if an individual is recognized, consistent with disclosed embodiments. In some embodiments, identification module 610 may be configured to perform some or all of process 700 to determine if an individual for which image data is received matches an individual for which face-identifying information is stored.

Identification module 610 may be configured to receive image data as it is received from sensory unit 120. Identification module 610 may process the received image data to determine the existence of face-identifying information in the image data (step 710). Identification module 610 may be configured to process images to identify portions of an image that are associated with a person present in the image, such as the person's face. Identification module 610 may be configured to identify, for example, typical size and/or proportions of a face and/or head, particular facial features and/or an arrangement of facial features, or any other information that indicates that the image includes a person's face.

Identification module 610 may proceed to communicate with database 630 to access the database of stored facial information (step 720). In some embodiments, identification module 610 and/or database 630 may be configured to perform one or more processes that provides identification module 610 with access to search database 630. For example, identification module 610 may generate a request for access to a portion of database 630 that stores facial information for the audible facial recognition function of apparatus 110.

After accessing database 630, identification module 610 may be configured to search the stored facial information by comparing the face-identifying information found in the image data with the stored facial information (step 730). In some embodiments, identification module 610 may be configured to perform one or more image- and/or data-matching processes that attempt to match some or all of face-identifying information identified in image data received from sensory unit 120 to facial information associated with a particular individual stored in database 630.

For example, identification module 610 may use one or more matching algorithms to search facial information associated with each individual stored in database 630. The matching algorithm may be configured in any manner that allows identification module 610 to compare received facial information with stored facial information and make a determination whether the results of the comparison indicate a match or if identification module 610 should move to facial information associated with the next stored person.

In some embodiments, database 630 may be configured to store statistical information associated with the audible facial recognition function of apparatus 110 in order to allow identification module 610 to take statistical information into account when comparing face-identifying information. The statistical information may include, for example, frequency of specific matches of facial information, information about relationships between specific individuals, information about a time of specific matches, sound recording, information about location of specific matches, etc. Identification module 610 may use the statistical information through use of a particular algorithm that indicates an order and/or priority for individuals to be searched. For example, identification may use a memory managing algorithm. The memory managing algorithm may use statistical information to determine an order of individuals to be searched while identification module 610 attempts to find a match for received face-identifying information.

One example of a memory managing algorithm may use statistical information associated with the time a match of facial information for a particular individual was last found. The memory managing algorithm may determine an order of individuals to search based on this statistical information. The order may include attempting to match facial information associated with an individual for which a match was most recently found first, followed by facial information associated with an information was most recently matched before the first individual, and so on until the individual for which facial information was least recently matched.

Regardless of the processes and/or algorithms used to search the database of facial information, identification module 610 may make a determination of whether a match was found (step 740). Identification module 610 may determine that a match has been found when stored facial information sufficiently matches the face-identifying information found in the real-time image data. Identification module 610 may be configured to make a determination of whether information sufficiently matches based on the results of one or more comparison processes and/or algorithms that determine a likelihood that the received face-identifying information and the particular stored facial information are associated with the same person.

In some embodiments, identification module 610 may be configured to stop search after finding facial information that sufficiently matches such that a likelihood of a match being correct is above a threshold value. In other embodiments, identification module 610 may be configured to search each individual in the database and select a match based on the facial information associated with an individual that has the highest likelihood of being a match.

In some embodiments, identification module 610 may be configured to use audio features to verify a potential match and/or find a match when no matching facial information is found. For example, apparatus 110 may be configured to capture and store audio features associated with the voice of individuals for which face-identifying information is stored in database 630 (although it should be understood that only audio features may be stored for some individuals). During execution of process 700, an input device associated with apparatus 110, such as a microphone, may capture an audio recording of the voice of an individual near the user (e.g., an individual in front of the user and found in the image data).

In some embodiments, after a potential match has been found using captured face-identifying information, identification module 610 may compare the captured audio recording to stored audio features of the associated individual's voice. If the comparison results in a match (e.g., sufficient similarity of audible features above a certainty threshold), the match of an associated individual may be verified. If the comparison does not result in a match, identification module 610 may continue to search database 630 for another potential match of face-identifying information. In other embodiments, if a match between captured face-identifying information and stored facial information is not found, the audio recording may be compared to audio features stored in database 630 to attempt to determine a match to identify an associated individual (e.g., an individual standing in front of the user).

Figure 8:
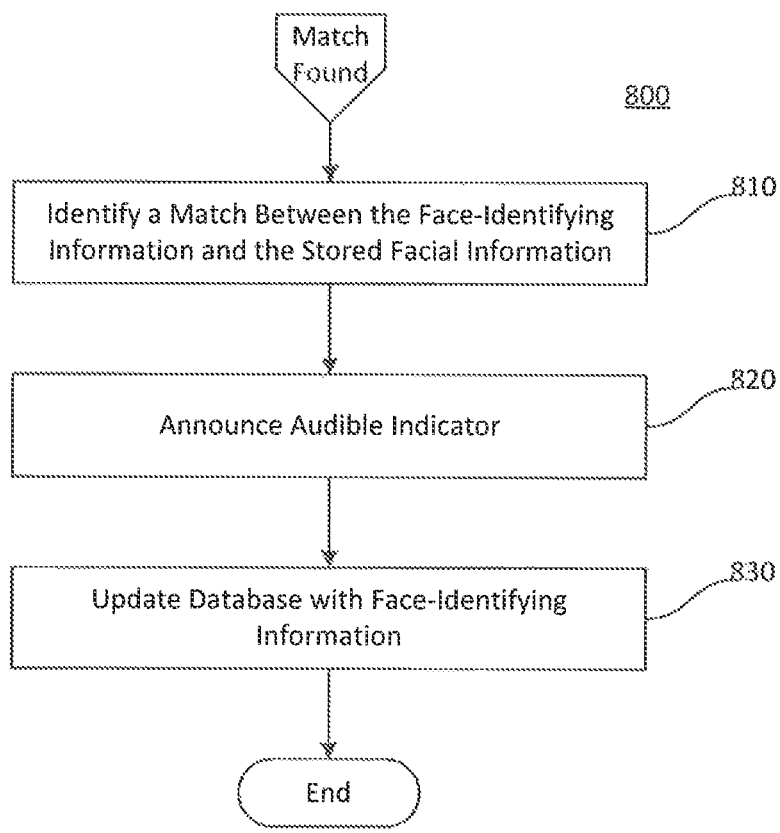
FIG. 8 is a flowchart of an example of a process that may be used in conjunction with the process of FIG. 7 when an individual is recognized.
Figure 9:
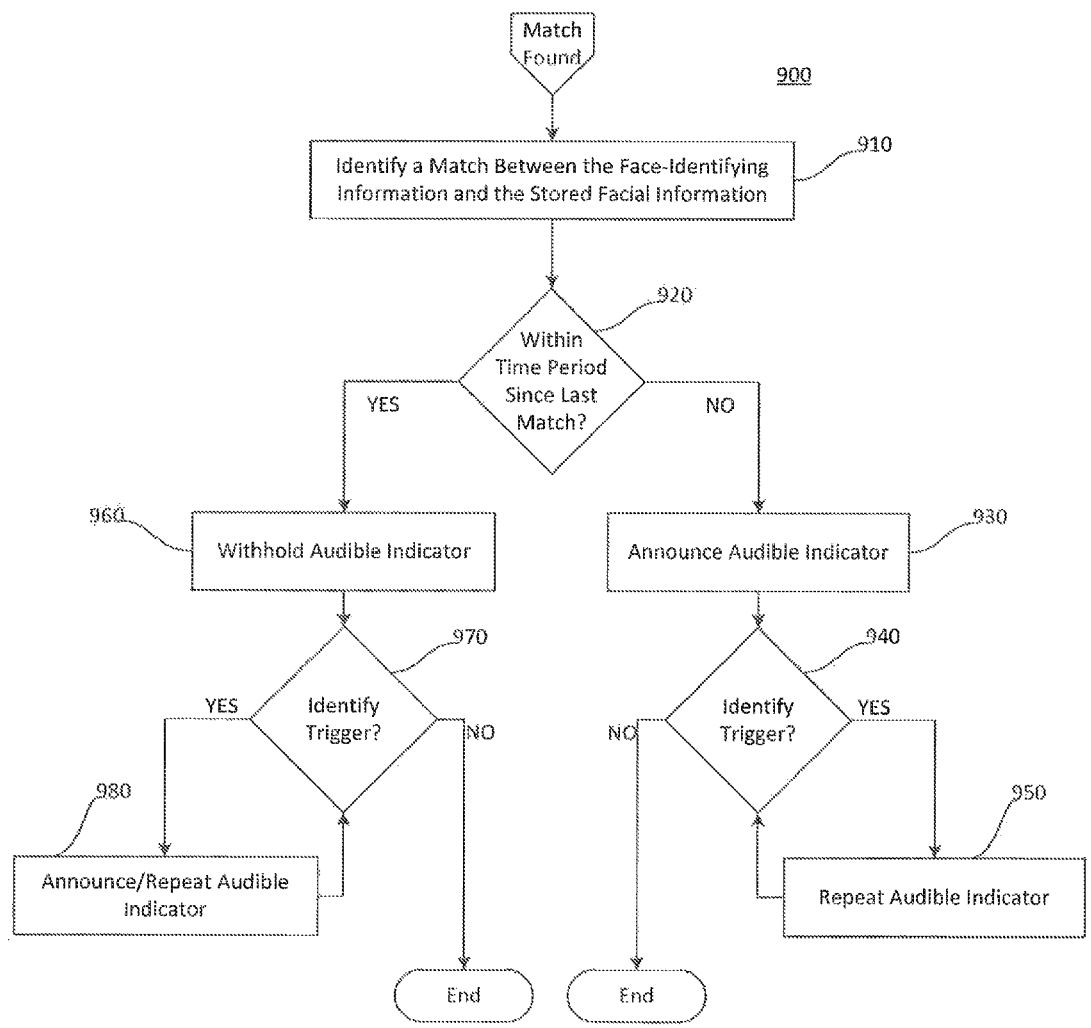
FIG. 9 is a flowchart of another example of a process that may be used in conjunction with the process of FIG. 7 when an individual is recognized.
Figure 10:
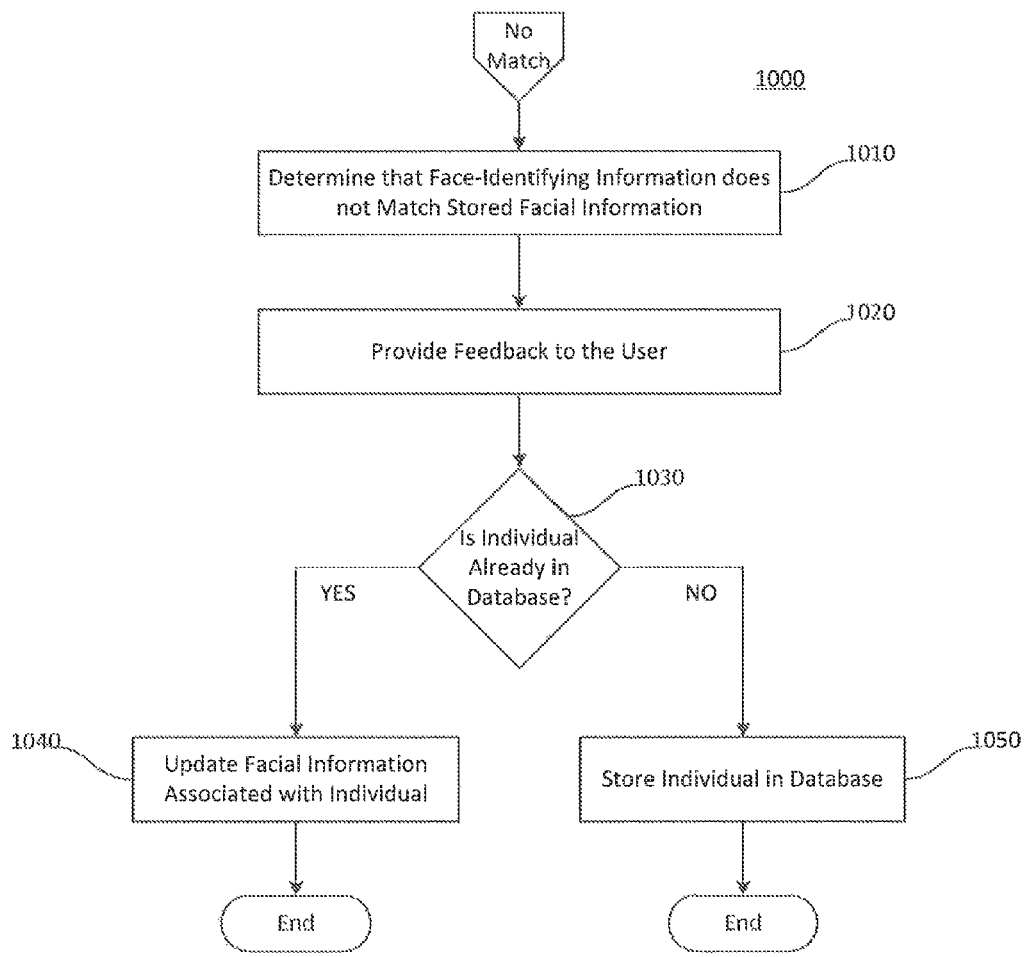
FIG. 10 is a flowchart of an example of a process that may be used in conjunction with the process of FIG. 7 when an individual is not recognized.

FIGS. 8 and 9 depict examples of processes that may be used after identification module 610 determines that a match has been found. However, it should be understood that, in some instances, identification module 610 may determine that the face-identifying information found in the image data does not match any stored facial information. FIG. 10 depicts an example of a process that may be used in such a scenario.

FIG. 8 depicts an example of a process 800, consistent with disclosed embodiments. In certain aspects, process 800 may be used in conjunction with process 700 in instances where a match was found in step 740 (e.g., a face identified in the real-time image data matches a face stored in the database of facial information). In these instances, identification module 610 may identify that there is a match between the received face-identifying information and the stored facial information (step 810).

In some situations, apparatus 110 (e.g., via process 700 and/or 800), may identify face-identifying information associated with more than one individual found in the image data (e.g., when two or more people are in front of a user of apparatus 110). Identification module 610 may be configured to determine that there is more than one face in the image data, and perform process 700 to determine if there is a match found for each face.

Feedback module 620 may receive information indicating that the match has been identified. For example, feedback module 620 may receive a notification from identification module 610. In some embodiments, the notification may include an audible indicator associated with the matched facial information. In other embodiments, the notification may cause feedback module 620 to access database 630 to retrieve an audible indicator associated with the matched facial information, or identification module 610 and/or feedback module 620 may perform some other process that results in receipt of information associated with the audible indicator.

Feedback module 620 may subsequently cause apparatus 110 (e.g., via feedback-outputting unit 340) to announce the audible indicator (step 820). Feedback module 620 may operate in conjunction with feedback-outputting unit 340 to provide the audible indicator to the user of apparatus 110. For example, apparatus 110 may generate an audible announcement via audio headphones or other speaker device. If matches are found for more than one face, feedback module 620 (and/or identification module 610) may be configured to determine which audible indicators to announce, and/or which order to announce them in, according to a pre-defined rule. For example, feedback module may announce each audible indicator in order of proximity to the user (e.g., closest individual identified first), or other order of priority (e.g., family members identified last).

Since the audible indicator may be associated with facial information matched to a face found in the image data, announcement of the audible indicator may indicate to the user of apparatus 110 an identity of a nearby person. In some embodiments, the audible facial recognition function of apparatus 110 may end after an audible identifier has been announced. However, as shown in FIG. 8, in some embodiments, process 800 may continue by further processing the received face-identifying information.

For example, identification module 610 may update database 630 with the face-identifying information found in the image data (step 830). For example, identification module 610 may be configured to store the face-identifying information as additional facial information associated with an individual whose facial image is already stored in database 630. In this way, the available information for that particular individual may be expanded to allow for more comprehensive matching of facial information. Similarly, identification module 610 may be configured to update stored facial information stored in database 630 with current facial information derived from the face identifying information in the real-time image data. In this way, the facial information associated with that particular individual may be updated to reflect changes in facial information, such as those due to aging, changes in style, etc.

FIG. 9 depicts an example of a process 900, consistent with disclosed embodiments. In some aspects, process 900 may be used in addition or as an alternative to process 800 in instances where a match was found in step 740 of process 700. As with process 800, process 900 may include identification module 610 identifying that there is a match between the received face-identifying information and the stored facial information (step 910).

However, in some embodiments, further processing of the match determination may depend on additional information. For example, whether or not an audible indicator is announced to a user of apparatus 110 may depend on how recent the same individual was matched and identified. In this way, apparatus 110 may be prevented from repetitively announcing the identity of an individual who frequently reappears in the image data (e.g., in instances where the user and the individual are interacting with each other).

To provide this functionality, feedback module 620 (and/or identification module 610) may determine, when a match is found, whether a predetermined time period has passed since the associated individual was initially and/or most recently identified (step 920). The predetermined time period may be any time period and may be selected based on any criteria. In some embodiments, the time period may be fixed for all situations. In other embodiments, the time period may depend on contextual and/or statistical information. In some embodiments, the time period may be selected by the user of apparatus 110.

If feedback module 620 determines that the match is not within the predetermined time period (step 920—NO), feedback module 620 may be configured to cause apparatus 110 to announce an audible indicator associated with the matched individual (step 930). Step 930 may correspond to step 820 of process 800 or some other step by which apparatus 110 informs the user of apparatus 110 of the identity (or some other information) of the individual associated with the matched facial information.

In some embodiments, process 900 may end after the audible indicator has been announced. In other embodiments, identification module 610 may proceed to add to and/or update database 630 with the received face-identifying information (e.g., step 830 of process 800). In still other embodiments, as shown in FIG. 9, process 900 may continue with feedback module 620 (and/or identification module 610) looking for additional input from the user.

For example, feedback module 620 may look for a trigger from the user of apparatus 110 (step 940). The trigger may be any indication from the user of a request to perform an additional action. In some embodiments, the trigger may be associated with the user's desire to repeat the audible indicator. The trigger may be in the form of any input, such as an indication detected by sensory unit 120. For example, the trigger may be a pointing finger viewed by image sensor 350, or a voice command. In some embodiments, the trigger may include use of function button 410.

If feedback module 620 identifies a trigger (step 940—YES), feedback module 620 may cause apparatus 110 to repeat the audible indicator to the user (step 950). Feedback module 620 may continue to look for triggers to repeat the audible indicator until it is determined that no additional triggers associated with that particular function are identified (step 940—NO), which may occur after a predetermined period of time, after the individual leaves the image data, etc.

In some instances, feedback module 620 may determine that a determined match of facial information occurred with the predetermined time period (step 920—YES). In these instances, feedback module 620 may withhold the audible identification of the individual (step 960). In this way, apparatus 110 may refrain from announcing an audible identifier when the associated individual is merely reappearing in the image data within a predetermined time period since the individual was initially identified.

As with step 930, process 900 may end after step 960, or it may be followed with an updating step (e.g., step 830). However, in some instances, process 900 may continue with feedback module 620 looking for a trigger (step 970). Step 970 may correspond to step 940 in that feedback module 620 may look for a trigger as any indication that the user is requesting that the apparatus perform an additional process. For example, the user may desire for the audible identifier to be announced, even though the identification is determined to be within the predetermined time period.

Feedback module 620 may identify a trigger associated with a user's desire to audibly re-identify (or initially identify) the associated individual during the predetermined time period (step 970—YES). As was described with respect to step 940, the trigger may take any form. For example, the trigger may include a pointing finger that is viewed by image sensor 350.

After feedback module 620 identifies the trigger, feedback module 620 may cause apparatus 110 to audibly re-identify (or initially identify) the associated individual during the predetermined time period (step 980). As with step 950, feedback module 620 may continue to look for triggers to repeat the audible indicator until it is determined that no additional triggers associated with that particular function are identified (step 970—NO), which may occur after a predetermined period of time, after the individual leaves the image data, etc. In some embodiments, feedback module 620 may recognize that an individual has walked away and came back, causing re-identification of the associated individual, regardless of a time limit.

In some instances, individuals that appear in the real-time image data may not match individuals for which facial information is stored in database 630. For example, the user of apparatus 110 may be in proximity to one or more persons that the user does not know or that the user knows but have not been stored in database 630. FIG. 10 depicts an example process 1000, consistent with disclosed embodiments. In some embodiments, process 1000 may follow process 700 in instances when no match was found for received face-identifying information.

After unsuccessfully searching stored facial information, identification module 610 may determine that face-identifying information does not match stored facial information (step 1010). In some aspects, identification module 610 may determine that the face-identifying information fails to match stored facial information with sufficient certainty to determine that the face associated with the face-identifying information is associated with an individual for which facial information is stored.

In some embodiments, feedback module 620 may be configured to provide feedback to the user of apparatus 110 to indicate that no match was found between the received face-identifying information and the stored facial information (step 1020). For example, feedback module 620 may receive a notification from identification module 610 indicating that no match was found, and feedback module 620 may perform one or more processes to notify the user. For example, feedback module 620 may communicate with feedback-outputting unit 340 to cause feedback-outputting unit 340 to notify the user (e.g., make an audible announcement). It should be understood that step 1020 may be optional and that in some embodiments, no feedback to the user may be provided.

In some embodiments, feedback module 620 (and/or identification module 610) may be configured to store the received face-identifying information in database 630. For example, feedback module 620 may be configured to store facial information and an audible indicator for a non-recognized individual (e.g., a person for which face-identifying information was identified in the image data, but for which not match in database 630 was found). In order to determine the face-identifying information is associated with the correct individual, feedback module 620 may determine if the face-identifying information is associated with an individual that is stored in database 630 (step 1030).

In some instances, even though a match was not found, the face-identifying information may be associated with an individual already stored in database 630, such as instances in which the individual's appearance has changed, or when the stored facial information is inaccurate or low-quality. Feedback module 620 may determine whether the individual is already stored in database 630 based at least in part on input from the user of apparatus 110. For example, the user may provide an audible indicator (e.g., via speech into a microphone) that feedback module 620 (and/or identification module 610) may determine matches a stored audible indicator associated with a stored individual.

If feedback module 620 determines that the face-identifying information is associated with an individual already stored in database 630 (step 1030—YES), feedback module 620 (and/or identification module 610) may store the face-identifying information to add to or update the stored facial information for that individual (step 1040). In this way, database 630 may be configured to store more comprehensive facial information that may lead to more accurate matching of facial information in subsequent situations.

However, if feedback module 620 determines that the face-identifying information is associated with an individual that is not stored in database 630 (step 1030—NO), feedback module 620 (and/or identification module 610) may be configured to store information associated with the non-recognized individual in database 630 (step 1050). For example, feedback module 620 may be configured to store facial information and an audible indicator for the non-recognized individual. In some embodiments, feedback module 620 may store facial information automatically and prompt the user of apparatus 110 to input an audible indicator to be associated with the individual. In other embodiments, feedback module 620 may store the facial information and the audible indicator for the non-recognized individual upon identifying a trigger in the image data associated with the user's desire to add the non-recognized individual to the at least one database. In some embodiments, the trigger may be a pointing finger (e.g., the user points at the non-recognized individual).

Through process 1000, a user of apparatus 110 may expand database 630 to store facial information associated with non-recognized individuals. Database 630 may be configured to grow and adapt to include a more comprehensive and current catalog of facial information and individuals associated with the facial information. In this way, apparatus 110 may be configured to provide an audible facial recognition function that improves and expands over time.

While processes 700, 800, 900, and 1000 have been described as examples, it should be understood that apparatus 110 may use any combination of these or any other processes to provide an audible facial recognition function. Additional or alternative functions of apparatus 110 may be used in conjunction with the audible facial recognition function to provide additional features to apparatus 110.

For example, in some embodiments, image sensor 350 may be configured to capture images in various resolutions. In performing one or more of processes 700, 800, 900, and 1000 (or any other process), identification module 610 (and/or feedback module 620) may be configured to operate in a lower power consumption mode. In some embodiments, the low power consumption mode may include determining an existence of face-identifying information in image data take at a resolution lower that a resolution of image data used to compare face-identifying information in the real-time image data with facial information stored in database 630.

In another example, in some embodiments, feedback module 620 (and or identification module 610) may be configured to look for a trigger from a recognized individual before audibly identifying that individual. For example, feedback module 620 may be configured to determine if an individual is looking in a direction of the user of apparatus 110. If it is determined that the individual is looking in a direction of the user of apparatus 110, feedback module 620 may cause apparatus 110 to audibly identify the individual. Feedback module 620 may perform this function for more than one recognized individual. For example, feedback module 620 may be configured to determine if two individuals are looking in a direction of the user of apparatus 110, and, if so, cause apparatus 110 to audibly identify both individuals.

The disclosed apparatus 110 may include the audible facial recognition function described herein in order to identify nearby individuals to a user of apparatus 110. User 110 may be a visually impaired user than may be unable to visually identify these individuals. Apparatus 110 may match detected faces to stored faces and provide audible feedback to assist these users in identifying people that are around them.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for aiding a visually impaired user to identify individuals, the apparatus comprising:
    a portable image sensor configured to be worn by the visually impaired user and to capture real-time image data from an environment of the user;
    a memory storing instructions; and
    at least one portable processor device configured to execute the instructions to:
    determine an existence of first face-identifying information in the real-time image data;
    access at least one database storing facial information associated with selected individuals and audible indicators of identities of the individuals;
    compare the first face-identifying information in the real-time image data with the stored facial information in the at least one database;
    identify a match between the first face-identifying information in the real-time image data and the stored facial information in the at least one database;
    based on the match, cause an audible indicator of an identity of an associated individual to be announced to the visually impaired user;
    determine that the first face-identifying information related to the associated individual is no longer present in the real-time image data;
    after the determination that the first face-identifying information related to the associated individual is rip longer present in the real-time image data, determine that new face-identifying information related to the associated individual appears in the real-time image data within a predetermined time period after the first face-identifying information was present in the real-time image data; and
    based on the determination that the new face-identifying information related to the associated individual appears in the real-time image data within the predetermined time period, withhold an audible identification of the associated individual.

2. The apparatus of claim 1, wherein the at least one processor device is further configured to process the image data to identify a trigger associated with a user's desire to audibly re-identify the associated individual during the predetermined period, and audibly re-identify the associated individual during the predetermined period.

3. The apparatus of claim 1, wherein the at least one processor device is further configured to repeat the audible indicator upon identifying a trigger associated with a user's desire to repeat the audible indicator.

4. The apparatus of claim 3, wherein the at least one processor device is further configured to process the image data to identify the trigger associated with a user's desire to repeat the audible indicator.

5. The apparatus of claim 4, wherein the trigger includes a pointing finger.

6. The apparatus of claim 1, wherein the at least one processor device is further configured to store facial information and an audible indicator for a non-recognized individual.

7. The apparatus of claim 6, wherein the at least one processor device is further configured to store the facial information and the audible indicator for the non-recognized individual upon identifying a trigger in the image data associated with a user's desire to add the non-recognized individual to the at least one database.

8. The apparatus of claim 7, wherein the trigger includes a pointing finger.

9. The apparatus of claim 1, wherein the at least one processor device is further configured to store additional facial information for an individual whose facial image is already stored in the database.

10. The apparatus of claim 1, wherein the at least one processor device is further configured to capture an audio recording of an individual's voice, and compare the captured audio recording to stored audio features of the associated individual's voice to verify the match.

11. The apparatus of claim 1, wherein the at least one processor device is further configured to capture an audio recording of a non-recognized individual's voice, compare the captured audio recording to stored audio features, and identify a match between the captured audio recording and stored audio features associated with an individual.

12. The apparatus of claim 1, wherein the at least one processor device is further configured to identify a match for two or more associated individuals in the real-time image data, and announce audible indicators associated with the two or more associated individuals according to a pre-defined rule.

13. The apparatus of claim 12, wherein the at least one processor device is further configured to determine an order in which to announce the audible indicators associated with the two or more individuals according to the pre-defined rule.

14. The apparatus of claim 1, wherein the at least one processor device is further configured to update the stored facial information in the at least one database with current facial information derived from the face-identifying information in the real-time image data upon identifying the match between the face-identifying information and the stored facial information.

15. The apparatus of claim 1, wherein the facial information of an individual, stored in the at least one database, is derived from multiple images of the individual.

16. The apparatus of claim 1, wherein the at east one processor device is further configured to provide feedback to the visually impaired user that no match was found between the face-identifying information and the stored facial information.

17. The apparatus of claim 1, wherein the image sensor is configured to capture images in various resolutions.

18. The apparatus of claim 17, wherein the at least one processor device is further configured to operate in a low power consumption mode by determining an existence of face-identifying information in image data taken at a resolution lower than a resolution of image data used to compare the face-identifying information in the real-time image data with the stored facial information in the at least one database.

19. The apparatus of claim 1, wherein the at least one processor device is further configured to implement a memory managing algorithm when comparing the face-identifying information with the stored facial information.

20. The apparatus of claim 19, wherein the at least one processor device is further configured to store statistical information associated with previous matches and to use the statistical information when implementing the memory managing algorithm.

21. The apparatus of claim 20, wherein the statistical information includes at least one of: information about a frequency of specific matches, information about relationships between specific individuals, information about a time of specific matches, sound recording, and information about location of specific matches.

22. The apparatus of claim 1, wherein the at least one processor device is further configured to determine if the associated individual is looking in a direction of the visually impaired user, and if it is determined that the associated individual is looking in a direction of the visually impaired user, audibly identify the associated individual.

23. The apparatus of claim 1, wherein the at least one processor device is further configured to determine if the associated individual and at least one other individual are looking in a direction of the visually impaired user, and if it is determined that the associated individual and the at least one other individual are looking in a direction of the visually impaired user, audibly identify the associated individual and the at least one other individual.

24. A non-transitory computer readable medium storing computer implementable instructions for carrying out a method for identifying individuals in an environment of a user, the method comprising:
receiving real-time image data from a portable image sensor configured to be worn by the user and to capture real-time image data from the environment of the user;
determining an existence of first face-identifying information in the real-time image data;
accessing at least one database storing facial information associated with selected individuals and indicators associated with identities of the selected individuals;
comparing the first face-identifying information in the real-time image data with the stored facial information in the at least one database;
identifying a match between the first face-identifying information in the real-time image data and the stored facial information in the at least one database;
outputting to the user an indicator of an associated individual;
determining that the first face-identifying information related to the associated individual is no longer present in the real-time image data;
after the determination that the first face-identifying, information related to the associated individual is no longer present in the real-time image data, determining that new face-identifying information related to the associated individual appears in the real-time image data within a predetermined time period after the first face-identifying information was present in the real-time image data; and
based on the determination that the newface-identifying information related to the associated individual appears in the real-time image data within the predetermined time period, withholding outputting of the indicator of the associated individual.

25. The software product of claim 24, wherein upon identifying a trigger associated with a user's desire to audibly re-identify the associated individual during the predetermined time period, re-outputting the indicator of the associated individual during the predetermined time period.

26. The software product of claim 24, wherein the indicator is an audible indicator.

* * * * *

UNITED STATES PATENT AND TRADEMARK OFFICE
CERTIFICATE OF CORRECTION

| | |
|---|---|
| PATENT NO. | : 9,025,016 B2 |
| APPLICATION NO. | : 14/135727 |
| DATED | : May 5, 2015 |
| INVENTOR(S) | : Yonatan Wexler et al. |

It is certified that error appears in the above-identified patent and that said Letters Patent is hereby corrected as shown below:

In the Claims

In Claim 1, column 24, lines 2-3, "individual is rip longer present" should read
--individual is no longer present--.

In Claim 2, column 24, lines 16-17, "during the predetermined period" should read
--during the predetermined time period--.

In Claim 2, column 24, line 18, "during the predetermined period" should read
--during the predetermined time period--.

In Claim 24, column 26, lines 35-36, "the newface-identifying information" should read
--the new face-identifying information--.

Signed and Sealed this
Twenty-second Day of September, 2015

Michelle K. Lee
*Director of the United States Patent and Trademark Office*